(12) United States Patent
Oberholzer

(10) Patent No.: US 8,410,278 B2
(45) Date of Patent: Apr. 2, 2013

(54) METHOD FOR PREPARING A NON-HYDRATABLE CRYSTAL FORM

(75) Inventor: Matthew Richard Oberholzer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 196 days.

(21) Appl. No.: 13/121,218

(22) PCT Filed: Nov. 11, 2009

(86) PCT No.: PCT/US2009/063991
§ 371 (c)(1),
(2), (4) Date: Mar. 28, 2011

(87) PCT Pub. No.: WO2010/056720
PCT Pub. Date: May 20, 2010

(65) Prior Publication Data
US 2011/0184183 A1    Jul. 28, 2011

Related U.S. Application Data

(60) Provisional application No. 61/114,629, filed on Nov. 14, 2008.

(51) Int. Cl.
*C07D 401/04* (2006.01)

(52) U.S. Cl. .................................................. 546/275.4

(58) Field of Classification Search ................ 546/275.4
See application file for complete search history.

(56) References Cited

U.S. PATENT DOCUMENTS 7,528,260 B2 * 5/2009 Shapiro et al. ............. 548/374.1

* cited by examiner

*Primary Examiner* — Patricia L Morris

(57) ABSTRACT

A method is disclosed for preparing a non-hydratable crystal form from a hydratable crystal form of 3-bromo-1-(3-chloro-2-pyridinyl)-N-[4-cyano-2-methyl-6-[(methylamino)-carbonyl]phenyl]-1H-pyrazole-5-carboxamide (Compound 1).

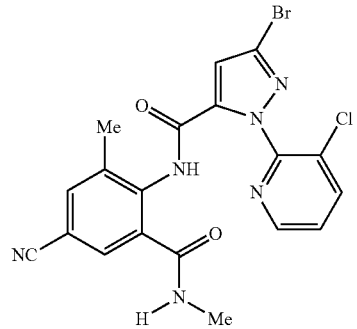

15 Claims, 2 Drawing Sheets

METHOD FOR PREPARING A NON-HYDRATABLE CRYSTAL FORM

FIELD OF THE INVENTION

This invention relates to a method for preparing a non-hydratable crystal form from a hydratable crystal form of 3-bromo-1-(3-chloro-2-pyridinyl)-N-[4-cyano-2-methyl-6-[(methylamino)carbonyl]phenyl]-1H-pyrazole-5-carboxamide.

BACKGROUND OF THE INVENTION

PCT Patent Publications WO 04/067528 and WO 06/062978 disclose methods for the preparation of 3-bromo-1-(3-chloro-2-pyridinyl)-N-[4-cyano-2-methyl-6-[(methylamino)-carbonyl]phenyl]-1H-pyrazole-5-carboxamide (Compound 1), as well as the utility of this compound as an insecticide. WO 06/062978 further discloses the purification of Compound 1 by recrystallization from 1-propanol.

It is well known in the art that certain crystalline compounds can exist as polymorphs. The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability.

Thus far, it has not been possible to predict the occurrence and number of crystalline polymorphs of any single compound, nor the particular physicochemical properties of any particular polymorph. Most importantly, thermodynamic stability and potentially different behavior after administration in living organisms cannot be determined in advance.

SUMMARY OF THE INVENTION

This invention is directed to a method for preparing Polymorph A of Compound 1 characterized by a X-ray diffraction pattern having at least the 2θ reflection positions 6.78, 11.09, 19.94, 20.99, 26.57, 26.98 and 31.52; comprising heating at a temperature between about 40° C. and the boiling point of the solvent a mixture comprising a solvent selected from the group consisting of water, n-heptane, 1-chlorobutane, toluene, 1-butanol and 1-pentanol, and Polymorph B of Compound 1 characterized by a X-ray diffraction pattern having at least the 2θ reflection positions 7.43, 9.89, 18.68, 19.36, 22.16, 23.09 and 25.70.

DETAILED DESCRIPTION OF THE INVENTION

Figure 1:
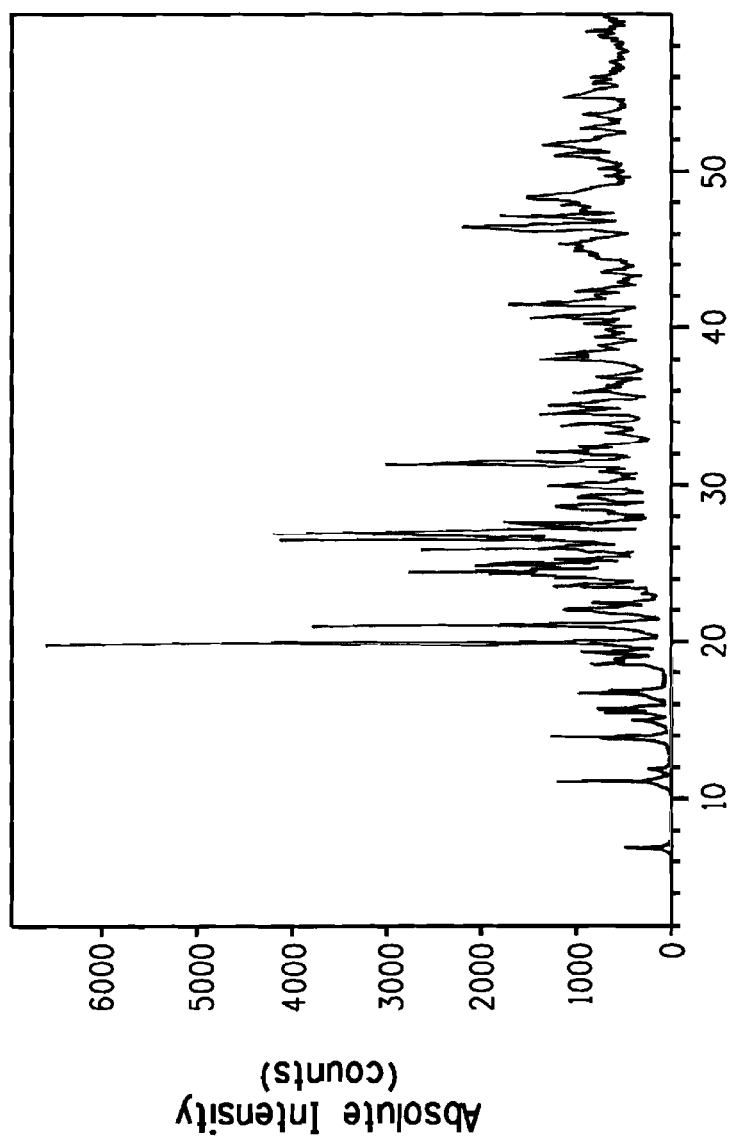
FIG. 1 is a powder X-ray diffraction pattern of Polymorph A of Compound 1 showing absolute intensity count graphed against 2θ reflection positions.

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Compound 1 is 3-bromo-1-(3-chloro-2-pyridinyl)-N-[4-cyano-2-methyl-6-[(methylamino)carbonyl]phenyl]-1H-pyrazole-5-carboxamide and has the following chemical structure:

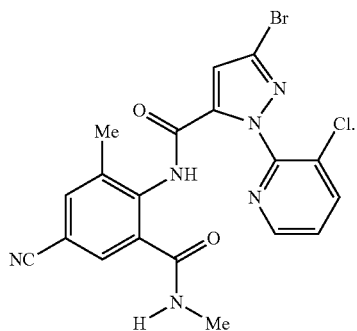

Compound 1 can exist in more than one crystal form (i.e. polymorph). One skilled in the art will appreciate that a polymorph of Compound 1 can exhibit beneficial effects (e.g., suitability for preparation of useful formulations, improved biological performance) relative to another polymorph or a mixture of polymorphs of the same Compound 1. Differences with respect to chemical stability, filterability, solubility, hygroscopicity, melting point, solid density and flowability can have a significant effect on the development of production methods and formulations, and the quality and efficacy of plant treatment agents.

A method has now been discovered for the preparation of a non-hydratable polymorph of Compound 1 (Polymorph A) from a hydratable polymorph of Compound 1 (Polymorph B) that typically is initially formed by procedures for preparing Compound 1. The water content of Polymorph B changes significantly on exposure to variations in atmospheric humidity. Unlike Polymorph B, Polymorph A does not gain or lose appreciable amounts of water when subjected to variations in atmospheric humidity. Moreover, Polymorph A does not typically convert to Polymorph B during long-term storage. This surprising stability facilitates a more consistent assay of Compound 1. These characteristics also make Polymorph A of Compound 1 well suited for the production of long-lasting stable solid formulations, enabling specifying a stable active ingredient content.

Furthermore, Polymorph A has a physical form enabling more efficient filtration compared to Polymorph B. During large-scale synthesis and isolation, the superior ease of separating Polymorph A can decrease process manufacturing costs.

Powder X-ray diffraction is used to identify the crystallized phases of both Polymorphs A and B of Compound 1. To characterize Polymorphs A and B, data were obtained with a Philips X'PERT automated powder diffractometer, Model 3040. Samples at room temperature were run in a batch mode with a Model PW 1775 or Model PW 3065 multi-position sample changer. The diffractometer was equipped with an automatic variable slit, a xenon proportional counter, and a graphite monochromator. The radiation was Cu (Kα), 45 kV, 40 mA. Samples were prepared as a dry smear on a low background glass specimen holder. Data were collected at 2θ angles from 2 to 60 degrees using a continuous scan with an equivalent step size of 0.03 degrees and a count time of 2.0 seconds per step. MDI/Jade software was used with the International Committee for Diffraction Data database for phase identification and comparison of diffraction patterns of the samples with those of reference materials.

The powder X-ray diffraction pattern of Polymorph A of Compound 1 is shown in FIG. 1. The corresponding 2θ values are tabulated in Table 1.

TABLE 1

2θ X-ray maxima for Polymorph A of Compound 1

| 2θ | 2θ | 2θ | 2θ | 2θ | 2θ |
|---|---|---|---|---|---|
| 6.78 | 19.94 | 27.59 | 34.64 | 41.54 | 50.87 |
| 11.09 | 20.99 | 28.39 | 35.21 | 42.38 | 51.77 |
| 11.82 | 22.01 | 28.70 | 36.02 | 42.97 | 52.91 |
| 13.90 | 22.53 | 29.27 | 36.32 | 43.62 | 53.60 |
| 14.76 | 23.60 | 29.96 | 36.98 | 44.69 | 54.81 |
| 15.42 | 24.14 | 31.04 | 38.03 | 45.32 | 55.73 |
| 15.73 | 24.44 | 31.52 | 38.42 | 45.62 | 56.21 |
| 16.61 | 24.89 | 32.13 | 39.44 | 46.46 | 57.09 |
| 18.55 | 26.03 | 32.59 | 39.77 | 47.16 | 58.64 |
| 18.89 | 26.57 | 33.30 | 40.19 | 48.29 | 59.00 |
| 19.31 | 26.98 | 33.86 | 40.70 | 50.24 | |

Figure 2:
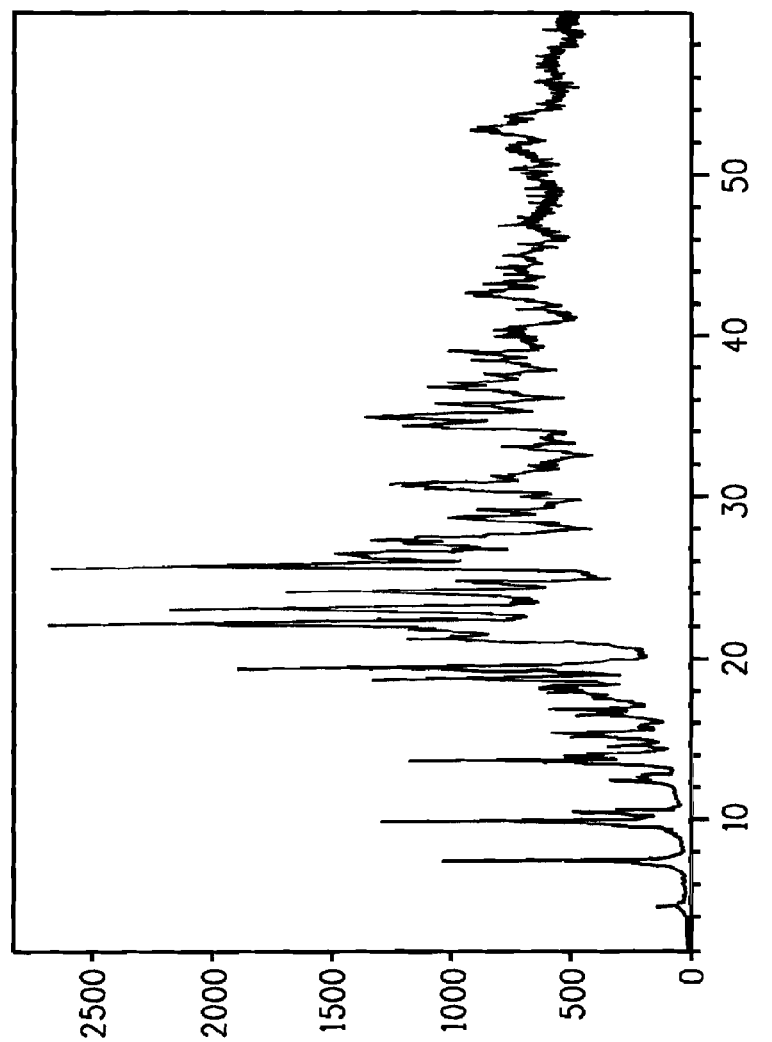
FIG. 2 is a powder X-ray diffraction pattern of Polymorph B of Compound 1 showing absolute intensity count graphed against 2θ reflection positions.

The powder X-ray diffraction pattern of Polymorph B of Compound 1 is shown in FIG. 2. The corresponding 2θ values are tabulated in Table 2.

TABLE 2

2θ X-ray maxima for Polymorph B of Compound 1

| 2θ | 2θ | 2θ | 2θ | 2θ | 2θ |
|---|---|---|---|---|---|
| 4.63 | 16.38 | 23.09 | 30.77 | 39.96 | 50.18 |
| 7.43 | 16.81 | 24.11 | 31.37 | 40.43 | 51.68 |
| 9.08 | 17.47 | 24.63 | 33.14 | 41.72 | 51.89 |
| 9.89 | 17.84 | 25.70 | 34.40 | 42.68 | 52.73 |
| 10.42 | 18.11 | 26.51 | 34.97 | 43.19 | 56.80 |
| 12.30 | 18.68 | 27.05 | 35.81 | 44.21 | 57.35 |
| 12.59 | 19.36 | 27.35 | 36.83 | 44.99 | |
| 13.64 | 21.17 | 28.73 | 37.16 | 46.88 | |
| 13.94 | 21.68 | 29.24 | 38.37 | 47.30 | |
| 15.28 | 22.16 | 30.50 | 38.96 | 49.76 | |

The crystalline polymorphs of Compound 1 can also be characterized by IR spectroscopy. IR spectra were measured on a FTS 3000 FTIR spectrometer (Varian, USA) using a Golden Gate ATR accessory for solids. The IR spectra contain the following band maxima shown in Table 3 (Polymorph A) and Table 4 (Polymorph B).

TABLE 3

IR band maxima for Polymorph A of Compound 1

| Wave numbers ($cm^{-1}$) | Wave numbers ($cm^{-1}$) | Wave numbers ($cm^{-1}$) |
|---|---|---|
| 3380 | 1490 | 1074 |
| 3125 | 1456 | 1044 |
| 3051 | 1419 | 1024 |
| 2242 | 1357 | 962 |
| 1691 | 1341 | 814 |
| 1633 | 1302 | 763 |
| 1587 | 1261 | |
| 1577 | 1229 | |
| 1544 | 1160 | |
| 1516 | 1132 | |

TABLE 4

IR band maxima for Polymorph B of Compound 1

| Wave numbers ($cm^{-1}$) | Wave numbers ($cm^{-1}$) | Wave numbers ($cm^{-1}$) |
|---|---|---|
| 3611 | 1533 | 801 |
| 3320 | 1467 | 799 |
| 3144 | 1358 | 752 |
| 3060 | 1303 | 668 |
| 2966 | 1274 | |
| 2942 | 1145 | |
| 2227 | 1077 | |
| 1672 | 1046 | |
| 1635 | 1028 | |
| 1594 | 962 | |

The crystalline polymorphs of Compound 1 can also be characterized and distinguished from each other by Raman and near infrared spectroscopy.

Embodiments of the present invention include:

Embodiment 1. The method described in the Summary of the Invention wherein the solvent is n-heptane.

Embodiment 1a. The method of Embodiment 1 wherein the temperature is between about 40 and about 100° C.

Embodiment 2. The method described in the Summary of the Invention wherein the solvent is toluene.

Embodiment 2a. The method of Embodiment 2 wherein the temperature is between about 40 and about 111° C.

Embodiment 3. The method described in the Summary of the Invention wherein the solvent is 1-chlorobutane or 1-chloropentane.

Embodiment 3a. The method described in the Summary of the Invention wherein the solvent is 1-chlorobutane.

Embodiment 3b. The method described in the Summary of the Invention wherein the solvent is 1-chloropentane.

Embodiment 3c. The method of Embodiment 3a wherein the temperature is between about 40 and about 77° C.

Embodiment 4. The method described in the Summary of the Invention wherein the solvent is 1-butanol or 1-pentanol.

Embodiment 4a. The method described in the Summary of the Invention wherein the solvent is 1-butanol.

Embodiment 4b. The method described in the Summary of the Invention wherein the solvent is 1-pentanol.

Embodiment 4c. The method of any one of Embodiments 4 through 4b wherein the temperature is between about 40 and about 100° C.

Embodiment 5. The method described in the Summary of the Invention wherein the solvent is water.

Embodiment 5a. The method of Embodiment 5 wherein the temperature is between about 60 and about 100° C.

Embodiment 5b. The method of Embodiment 5a wherein the temperature is between about 70 and about 100° C.

Embodiment 5c. The method of Embodiment 5a wherein the temperature is between about 70 and about 90° C.

Embodiment 5d. The method of any one of Embodiments 5 through 5c wherein the mixture is heated for at least about 2 hours.

Embodiment 5e. The method of Embodiment 5d wherein the mixture is heated for not more than about 48 hours.

Embodiment 5f. The method of Embodiment 5e wherein the mixture is heated for not more than about 24 hours.

Embodiment 5g. The method of Embodiment 5f wherein the mixture is heated for not more than about 12 hours.

Embodiment 6. The method of any one of Embodiments 5 through 5g wherein the mixture consists of at least about 30% water by weight.

Embodiment 6a. The method of Embodiment 6 wherein the mixture consists of at least about 40% water by weight.

Embodiment 6b. The method of Embodiment 6a wherein the mixture consists of at least about 80% water by weight.

Embodiment 6c. The method of Embodiment 6b wherein the mixture consists of at least about 90% water by weight.

Embodiment 6d. The method of Embodiment 6c wherein the mixture consists of at least about 95% water by weight.

Embodiment 6e. The method of Embodiment 6d wherein the mixture consists of at least about 98% water by weight.

Embodiment 7. The method described in the Summary of the Invention or any one of Embodiments 1 through 6e wherein about 0.1-10% by weight of Polymorph A (of Compound 1), relative to the weight of Polymorph B, is added to the mixture prior to heating.

Embodiment 7a. The method of Embodiment 7 wherein about 0.2-5% by weight of Polymorph A (of Compound 1), relative to the weight of Polymorph B, is added to the mixture prior to heating.

Polymorph B of Compound 1 can be converted to Polymorph A of Compound 1 by heating in the presence of a liquid phase comprising a solvent selected from certain organic solvents (i.e. solvents whose molecules contain at least one carbon atom). Only certain organic solvents are satisfactory for this conversion and prediction beyond close homologs is not possible, and thus identifying suitable classes of organic solvents requires experimentation. However, classes of organic solvents that generally work well for conversion of Polymorph B to Polymorph A have been found to include $C_3$-$C_8$ n-alkyl alcohols (e.g., n-propanol, n-butanol, n-pentanol), $C_4$-$C_6$ n-alkyl chlorides (e.g., n-butyl chloride or n-pentyl chloride), $C_6$-$C_{10}$ alkanes (e.g., n-hexane, hexanes, n-heptane, heptanes), $C_6$-$C_{10}$ cycloalkanes optionally substituted with up to 2 substituents independently selected from $C_1$-$C_2$ alkyl (e.g, cyclohexane, methylcyclohexane, cycloheptane), and benzene optionally substituted with up to 3 groups independently selected from $C_1$-$C_2$ alkyl (e.g., benzene, toluene, xylene). As Polymorph B typically comprises water (as water of hydration and residual water present in, for instance, a wet cake) and Polymorph A is anhydrous, water is liberated during the conversion. Azeotropic distillation can often be used to remove water from the polymorph conversion mixture.

Remarkably water is now discovered to work very well as a solvent in the heated liquid phase for converting Polymorph B to Polymorph A. This is particularly unexpected, because Polymorph B, which can accommodate significant amounts of water in its crystal lattice, can be anticipated to be favored over anhydrous Polymorph A in an aqueous medium. Nevertheless, water is now found to be particularly suitable in forming the liquid phase for conversion of Polymorph B to Polymorph A. Conversion proceeds to near 100% completion and in high yields within commercially convenient time periods at temperatures not exceeding about 100° C. (i.e. the normal boiling point of water). Not only is water much less expensive than organic solvents, but because Polymorph A has little solubility in water, it can be easily isolated by filtration. Alternatively if Polymorph A is in high concentration in water, Polymorph A can be isolated by evaporation of the water. Unlike organic solvents, water evaporated from the mixture does not need to be trapped.

In one embodiment of the present method, the mixture comprising Polymorph B and water (together with increasing amounts of Polymorph A) consists of a solid phase comprising decreasing amounts of Polymorph B and increasing amounts of Polymorph A, together with a liquid phase comprising water and optionally other solvents. Typically the optional other solvents are selected from organic solvents soluble in water, although organic solvents having low water solubility can be used as well. Therefore typically the liquid phase of the mixture in this embodiment of the present method consists of at least about 50%, and more typically at least about 80%, 90% or 95% and most typically at least about 98% water by weight.

The method of the embodiment described above provides a means of converting Polymorph B of Compound 1 to Polymorph A of Compound 1 by heating a mixture comprising Polymorph B of Compound 1 and water. Typically, a mixture of solid Polymorph B of Compound 1 and water, in the form of a suspension or slurry, is placed inside a suitably sized vessel equipped with means of mixing and heating the mixture. The mixture is then heated with mixing for a period of time long enough to complete the conversion of Polymorph B to Polymorph A. Mixing methods can be internal (e.g., a stir bar or an overhead stirrer) or external (e.g., rotating or shaking the reaction vessel). It is usually advantageous to add seed crystals of Polymorph A to the Polymorph B-containing mixture prior to heating. The addition of seed crystals reduces the total conversion time, and in some cases, reduces the temperature needed for the conversion to occur. After conversion of Polymorph B to Polymorph A, the mixture is cooled and the product isolated. Depending upon the relative amounts of the solid and liquid phases, product isolation can involve further drying of a slurry, or, if the mixture is a suspension, filtration followed by optional washing and then drying.

The amount of water in the mixture can be varied to accommodate different process equipment. For example, use of a large excess of water (i.e. where the water is a liquid phase in which the Polymorph B crystals are suspended) provides ease of stirring with conventional equipment such as an overhead stirrer. This suspension, however, requires significant energy to heat to the desired temperature. After the conversion to Polymorph A of Compound 1 is complete, the suspension can be filtered to isolate the solid product. This wet solid product, or wet cake, can be further dried to obtain a crystalline product suitable for preparing formulation compositions not including water or used directly to prepare aqueous formulation compositions (e.g., aqueous suspension concentrates).

A preferred embodiment of the present method comprises preparing the mixture of Polymorph B of Compound 1 and water as a slurry containing only the amount of water necessary to facilitate mixing. The use of less water is advantageous because less energy is required to heat the slurry to the desired temperature. In addition, a separate filtration step to isolate the Polymorph A crystals is not necessary, as the Polymorph A crystals can be isolated simply by drying the slurry. Depending upon the configuration of the vessel use for the conversion of Polymorph B to Polymorph A, it can be advantageous to perform this drying process directly in the vessel itself. In large-scale commercial processes, obviating the need to transfer a solid from one container to another results in significant cost savings. Alternatively, the Polymorph A crystals can be transferred to another vessel suitable for further drying.

Therefore, in a preferred embodiment of this invention, the crystals of Polymorph B of Compound 1 are combined with water to form a slurry which typically contains about 20-60% by weight water content, more typically 30-50% by weight water content, and most typically about 40% by weight water content.

Without further elaboration, it is believed that one skilled in the art using the preceding description can utilize the present invention to its fullest extent. The following Examples are, therefore, to be construed as merely illustrative and not limiting of the disclosure in any way whatsoever. The starting material for each Example may not have necessarily been prepared by the same preparative run. Percentages are by weight except where otherwise indicated.

Specific examples of the conversion of Polymorph B of Compound 1 to Polymorph A of Compound 1 are given below.

EXAMPLE 1

Preparation of Polymorph A of Compound 1 (Using a Slurry in Water)

A 250-mL, flat-bottomed jacketed cylindrical reactor (approximately 6 cm inner diameter, Wilmad-LabGlass) was charged with a water-wet cake of Polymorph B of Compound 1 (67.8 g, obtained following the procedure of Example 15 in PCT Patent Publication WO 06/062978, except the isolated product cake was washed with additional water; the water-wet cake was not dried and was used without further processing). The water-wet cake had a total moisture content of approximately 40% by weight, including approximately 1% residual acetonitrile. To the reactor was then added as seed crystals 2.0 g of Polymorph A of Compound 1 (prepared by heating and azeotropically drying a slurry of Polymorph B in heptane; 97.4% Polymorph A by near-IR analysis). Overhead agitation was installed using a glass, four-blade, 45-degree pitch impeller with an overall diameter of 4.5 cm and a projected blade height of approximately 2.2 cm. The reactor lid was attached and a thermocouple was inserted through one lid opening. All other lid openings were stoppered to prevent evaporation of moisture from the mixture. Agitation was started at approximately 21 revolutions per minute. Hot oil from a recirculating heater/chiller set to maintain 83° C. was circulated through the jacket of the reactor, and the reactor contents were allowed to heat and mix for 6.25 h, after which time the reactor contents were cooled and allowed to sit without mixing overnight. The following day, heating and mixing were restarted using the same conditions and maintained for 7.25 h. Samples were withdrawn from the reactor during the heating periods after stopping the agitation and removing the reactor lid. Before taking each sample, the reactor contents were thoroughly mixed manually with a spatula to ensure uniformity. A sample weighing between 1 and 3 g was withdrawn and then placed in a vacuum oven and dried overnight at approximately 50° C. and 17-40 kPa under a slight flow of nitrogen. The sample was then analyzed for crystal form by near-IR analysis. Crystal form assay results for the samples were as follows:

TABLE 5

| Conversion of Polymorph B to Polymorph A | |
|---|---|
| Time (h) | % Polymorph A (a) |
| 2 | 29.8 |
| 3 | 60.1 |
| 6.25 | 85.5 |
| 8.5 | 96.1 |
| 10.5 | 96.9 |
| 13.5 | 97.2 |

(a) as determined by near-IR analysis

After heating for a total of 13.5 h, the reactor was cooled to 25° C. and the contents of the reactor were transferred to a drying dish and dried overnight in a vacuum oven at 50° C. and 17-40 kPa under a slight flow of nitrogen to yield 28.2 g of dried Polymorph A of Compound 1 (92.3% pure by HPLC assay, 0.1% H$_2$O by Karl Fisher titration).

EXAMPLE 2

Preparation of Polymorph A of Compound 1 (Using a Suspension in Water)

A 100-mL round-bottom flask was charged with Polymorph B of Compound 1 (5.00 g, prepared according to the procedure of Example 15 in PCT Patent Publication WO 06/062978 without recrystallization from 1-propanol, 4.2% Polymorph A by near-IR analysis), Polymorph A of Compound 1 (prepared according to the procedure of Example 15 in WO 06/062978 including recrystallization from 1-propanol, 0.05 g, 97.0% Polymorph A by near-IR analysis) and water (15 mL). The mixture was rotated for 4 h in a water bath heated to 70° C. After cooling to 25° C., the mixture was filtered, washed with a few small portions of water, and dried in a vacuum oven at 60° C. and 17-40 kPa to afford Polymorph A of Compound 1 (96.8% Polymorph A by near-IR analysis), 4.74 g (93.9% recovery), melting 218-220° C.

EXAMPLE 3

Preparation of Polymorph A of Compound 1 (Using a Suspension in n-Heptane)

A 6-L glass jacketed cylindrical reactor fitted with overhead stirring, a thermocouple, a sampling diptube, nitrogen inlet, a distillation reflux head and a reflux condenser cooled by a closed-loop circulating chiller filled with 50:50 glycol:water fluid was charged with Polymorph B of Compound 1 (906.1 g of water-wet cake, approximately 40% moisture determined by weight loss after drying; prepared according to the procedure of Example 15 in PCT Patent Publication WO 06/062978 without recrystallization from 1-propanol, and without drying; polymorph B as determined by X-ray diffraction). The chiller temperature was set to 5° C. After flushing the reactor with nitrogen, the reactor was charged with 500 mL of fresh n-heptane and 2000 mL of n-heptane filtrate recycled from identical procedures as described in the present example. The reactor was flushed with nitrogen again, stirring was started, and the reaction mixture was heated to a jacket setpoint of 97.5° C. The reaction mixture began to boil when the mixture temperature reached approximately 80° C. at atmospheric pressure, and the condensate (i.e., condensed vapors) were directed from the reflux condenser take-off to a 1000 mL graduated cylinder modified with a bottom take-off. The condensate formed two separate clear liquid layers. The lower layer of the condensate, which was comprised of water, was periodically removed from the graduated cylinder and weighed. Approximately 350 mL of fresh n-heptane was added back to the reactor to compensate for the loss of n-heptane removed via the condensate collection cylinder. The reaction mixture temperature rose gradually as the water was removed from the system. When the reaction mixture temperature reached 90° C., the jacket setpoint was raised to 110° C., and the reaction mixture was heated to reflux for approximately two additional hours. Samples of the reaction mixture were taken periodically through the sample diptube. These samples were filtered, the resulting wet cake was recovered, dried in a vacuum oven, and assayed by near-IR analysis. Crystal form assay results for the samples were as follows:

TABLE 6

Conversion of Polymorph B to Polymorph A

| Time (min) (a) | Slurry temp (° C.) | % Polymorph A (b) |
| --- | --- | --- |
| 289 | 87.5 | 82.8 |
| 319 | 95.2 | 85.5 |
| 349 | 97.9 | 96.1 |
| 409 | 98.7 | 97.4 |

(a) as determined from the start of condensate appearance
(b) as determined by near-IR analysis The total volume of the aqueous layer removed from the distillate was 363 mL. The reactor was cooled to 25° C. and allowed to stand overnight. The reaction mixture was briefly stirred to aid in the discharge of the crystal slurry into a coarse glass fritted filter funnel, and the slurry was vacuum filtered. The filtrate was recycled and used to rinse residual product from the reactor into the filter. The wet cake was dried in a vacuum oven overnight at 80° C. under a slight nitrogen bleed to yield 529.5 g of product. The dried product was found to be Polymorph A by near-IR analysis and X-ray diffraction (97.1% Polymorph A by near-IR analysis).

EXAMPLE 4

Preparation of Polymorph A of Compound 1 (Using a Suspension in 1-Chlorobutane)

A glass screw-cap vial was charged with Polymorph B of Compound 1 (0.509 g), Polymorph A of Compound 1 (0.503 g, prepared from Polymorph B by a process similar to Example 3) and 1-chlorobutane (5.8 g). A magnetic stir bar was added, and the vial was capped. The vial was placed in an aluminum tray on top of a heated magnetic stir plate. The aluminum tray was heated to 45° C., and the reaction mixture was stirred at this temperature for approximately 27 hours. The reaction mixture was then filtered through a Büchner funnel using vacuum. The filter cake was air dried for approximately 30 minutes and then transferred to a new glass vial. The vial was covered with cloth and placed in a vacuum oven maintained at 60-70° C. and 17-40 kPa for approximately 3 days. The dried solids were analyzed by near-IR and found to be 97.4% Polymorph A.

EXAMPLE 5

Preparation of Polymorph A of Compound 1 (Using a Suspension in Toluene)

A 1000 mL glass cylindrical jacketed reactor fitted with overhead stirring, a Dean-Stark trap and reflux condenser, a thermocouple and an addition funnel was charged with Polymorph B of Compound 1 (100 g, obtained following the procedure of Example 15 in PCT Patent Publication WO 06/062978, except the isolated product cake was reslurried in an acetonitrile/water mixture, filtered and dried; Polymorph B was confirmed by X-ray diffraction). After flushing the reactor with nitrogen, the reactor was charged with 500 mL of toluene, and the reactor contents were mixed to form a slurry. The slurry was heated by raising the temperature of the jacket fluid to 120° C. Condensate began collecting when the slurry reached 102.6° C. and was collected in the Dean-Stark trap. After approximately one hour at reflux, 4.4 g of the lower (aqueous) layer was removed from the trap. After a further twenty minutes, the slurry appeared to be thinner and consisted of large solid particles that rapidly settled to the reactor bottom when the stirring was temporarily stopped. After approximately a total time of two hours at reflux, the reaction mixture was cooled to 20° C. The reaction mixture was discharged and filtered using vacuum to yield a wet cake that had the appearance of sand. The product cake was washed with a total of 150 mL of fresh toluene in two portions and then transferred to a drying dish. The product cake was dried in a vacuum oven at 100° C. and 17-40 kPa with a slight nitrogen bleed for three days. The dried product was determined to be Polymorph A of Compound 1 (92.2 grams) by X-ray diffraction; near-IR analysis showed the product to be 95.6% Polymorph A.

EXAMPLE 6

Preparation of Polymorph A of Compound 1 (Using a Suspension in 1-Butanol)

A glass screw-cap vial was charged with Polymorph B of Compound 1 (0.572 g), Polymorph A of Compound 1 (0.578 g, prepared from Polymorph B by a process similar to Example 3) and 1-butanol (4.0 g). A magnetic stir bar was added, and the vial was capped. The vial was placed in an aluminum tray on top of a heated magnetic stir plate. The aluminum tray was heated to 60° C., and the reaction mixture was stirred at this temperature for approximately 24 hours. The reaction mixture was then filtered through a Büchner funnel using vacuum. The filter cake was air dried for approximately 30 minutes and then transferred to a new glass vial. The vial was covered with cloth and placed in a vacuum oven at approximately 60° C. and 17-40 kPa for approximately 3 days. The dried solids were analyzed by near-IR and found to be 96.7% Polymorph A.

EXAMPLE 7

Preparation of Polymorph A of Compound 1 (Using a Suspension in 1-Pentanol)

A glass screw-cap vial was charged with Polymorph B of Compound 1 (0.611 g), Polymorph A of Compound 1 (0.605 g, prepared from Polymorph B by a process similar to Example 3) and 1-pentanol (4.0 g). A magnetic stir bar was added, and the vial was capped. The vial was placed in an aluminum tray on top of a heated magnetic stir plate. The aluminum tray was heated to 60° C., and the reaction mixture was stirred at this temperature for approximately 24 hours. The reaction mixture was then filtered through a Büchner funnel using vacuum. The filter cake was air dried for approximately 30 minutes and then transferred to a new glass vial. The vial was covered with cloth and placed in a vacuum oven maintained at approximately 60° C. and 17-40 kPa for approximately 3 days. The dried solids were analyzed by near-IR and found to be 97.2% Polymorph A.

What is claimed is:

1. A method for preparing Polymorph A of 3-bromo-1-(3-chloro-2-pyridinyl)-N-[4-cyano-2-methyl-6-[(methylamino)carbonyl]phenyl]-1H-pyrazole-5-carboxamide characterized by a X-ray diffraction pattern having at least the 2θ reflection positions

| 2θ |
| --- |
| 6.78 |
| 11.09 |
| 19.94 |
| 20.99 |
| 26.57 |
| 26.98 |
| 31.52 | comprising heating at a temperature between about 40° C. and the boiling point of the solvent a mixture comprising a solvent selected from the group consisting of water, n-heptane, 1-chlorobutane, toluene, 1-butanol and 1-pentanol, and Polymorph B of 3-bromo-1-(3-chloro-2-pyridinyl)-N-[4-cyano-2-methyl-6-[(methylamino)carbonyl]phenyl]-1H-pyrazole-5-carboxamide characterized by a X-ray diffraction pattern having at least the 2θ reflection positions

| 2θ |
| --- |
| 7.43 |
| 9.89 |
| 18.68 |
| 19.36 |
| 22.16 |
| 23.09 |
| 25.70. |

2. The method of claim 1 wherein the solvent is n-heptane.

3. The method of claim 1 wherein the solvent is toluene.

4. The method of claim 1 wherein the solvent is 1-chlorobutane.

5. The method of claim 1 wherein the solvent is 1-butanol or 1-pentanol.

6. The method of claim 1 wherein the solvent is water.

7. The method of claim 6 wherein the temperature is between about 60 and about 100° C.

8. The method of claim 7 wherein the temperature is between about 70 and about 100° C.

9. The method of claim 8 wherein the temperature is between about 70 and about 90° C.

10. The method of claim 6 wherein the mixture is heated for at least about 2 hours.

11. The method of claim 10 wherein the mixture is heated for not more than about 48 hours.

12. The method of claim 11 wherein the mixture is heated for not more than about 24 hours.

13. The method of claim 12 wherein the mixture is heated for not more than about 12 hours.

14. The method of claim 6 wherein about 0.1-10% by weight of Polymorph A relative to the weight of Polymorph B is added to the mixture prior to heating.

15. The method of claim 14 wherein about 0.2-5% by weight of Polymorph A relative to the weight of Polymorph B is added to the mixture prior to heating.

* * * * *